United States Patent [19]

Miyasaka et al.

[11] Patent Number: 4,950,405
[45] Date of Patent: Aug. 21, 1990

[54] FUNCTIONAL THIN ORGANIC MEMBRANE

[75] Inventors: Tsutomu Miyasaka; Yukio Maekawa; Hisashi Okamura, all of Kanagawa, Japan

[73] Assignee: Fuji Photo Film Co., Ltd., Kanagawa, Japan

[21] Appl. No.: 423,640

[22] Filed: Oct. 18, 1989

Related U.S. Application Data

[62] Division of Ser. No. 138,773, Dec. 29, 1987, abandoned.

[30] Foreign Application Priority Data

Dec. 29, 1986 [JP] Japan .................................. 61-315542

[51] Int. Cl.$^5$ ............................................. B01D 61/00
[52] U.S. Cl. ........................... 210/500.28; 210/500.33; 210/500.37; 210/500.4; 210/500.41
[58] Field of Search ........... 210/500.1, 500.21, 500.27, 210/500.28, 500.33, 500.37, 500.38, 500.39, 500.4, 500.41; 264/298

[56] References Cited

U.S. PATENT DOCUMENTS 4,632,800 12/1986 Barraud et al. ...................... 264/298

Primary Examiner—Frank Sever
Attorney, Agent, or Firm—Sughrue, Mion, Zinn, Macpeak & Seas

[57] ABSTRACT

A functional thin organic membrane comprising a monomolecular film which contains at least one organic amphoteric host molecule having a reactive functional group capable of chemically binding with a nucleophilic functional group at room temperature.

18 Claims, 1 Drawing Sheet

FUNCTIONAL THIN ORGANIC MEMBRANE

This is a division of application Ser. No. 07/138,773, filed 12/29/87, now abandoned.

FIELD OF THE INVENTION

The present invention relates to a thin organic membrane comprising organic molecules having chemically reactive functional groups. More particularly, the present invention relates to a reactive thin organic membrane capable of reacting with a nucleophilic amino compound such as an amino acid to fix the amino compound or immobilize the same at high density on the thin organic membrane through chemical bonds.

BACKGROUND OF THE INVENTION

As described in *J. Am. Chem. Soc.*, vol. 57, page 1007 (1935), monomolecular or multi-layered films prepared by the Langumuir-Blodgett method have the nature of ultra-thin films or two-dimensional crystals in which organic molecules are densely packed in a one-dimensionally oriented manner. Because of the capabilities provided by their characteristic nature, such ultra-thin films or two-dimensional crystals have been extensively used in practice as molecular devices.

The monomolecular film forming compounds which are suitable for the Langumuir-Blodgett method are amphoteric molecules, or molecules of the surfactant type which possess both hydrophilic and hydrophobic groups simultaneously. Commonly used amphoteric molecules are those having, as hydrophilic groups, organic groups or metal chelates containing acids, alcohols, esters, ethers, amines, etc. and having as hydrophobic groups, hydrophobic long-chain alkyl groups. When these amphoteric compounds as dissolved in organic solvents are spread over the surface of water, their molecules will diffuse over the liquid surface and become oriented to form a monomolecular film with the hydrophilic groups directed into water with the hydrophobic groups facing in the opposite direction. If this monomolecular film is compressed in a two-dimensional plane, it passes through a stage where it forms a two-dimensional liquid body, and thereafter the molecules are closely packed to form a stable solid film.

The formation of a stable monomolecular film in which the molecules are arranged in an orderly fashion is only possible with a molecular structure of the surfactant type described above. In the case of a non-surfactant type structure in which all of the molecules are hydrophobic, the molecules cannot be arranged in a desired way without causing agglomeration and it is difficult to provide a stable surface pressure in the structure. It is, therefore, important from a standpoint of molecular design of a monomolecular film forming compound that the compound be well balanced between the hydrophilic and hydrophobic groups and that it should be water-insoluble and non-volatile.

One of the features of such a monomolecular film that distinguish it from a so-called amorphous cast type film is that one surface of the monomolecular film is entirely occupied by hydrophobic groups while the other surface is entirely occupied by hydrophilic groups and that these groups are present at high density in each respective surface plane of the film. By utilizing this feature, the surface of a hydrophilic or hydrophobic substrate can be uniformly covered with such a monomolecular film with the hydrophilic groups being adsorbed on a hydrophilic substrate or the hydrophobic groups adsorbed on a hydrophobic substrate. If desired, a plurality of monomolecular films can be alternately built up on substrates by utilizing such molecular adsorption between hydrophilic groups or between hydrophobic groups. Such a resulting multi-layered film may also be characterized as an organic membrane in which the surface of its topmost layer is entirely covered with exposed hydrophilic or hydrophobic groups which are arranged at high density.

Methods are widely known in which a dissimilar guest compound is embedded in the surface or the interior of such a thin organic membrane having the construction described above and which supports the guest compound by utilizing the hydrophilic-hydrophilic and/or hydrophobichydrophobic interactions. In one of these methods, a dissimilar guest compound is mixed with a host compound in a solvent prior to film formation and the solution is then thinly spread to form a mixed monomolecular film. In this method, the guest compound is located between host compounds which serve as spacer molecules, so the amount of surface space occupied by the guest compound is far smaller than unity and the surface concentration of the guest compound is limited to a very low value. In another method, a monomolecular film of host molecules is first formed on the surface of water or a substrate and thereafter guest molecules are supplied from the aqueous phase (subphase) side in such a way that they are attached to, or incorporated in, the monomolecular film by means of diffusion and adsorption. In this case, the adsorption of the guest molecules is generally accomplished by the hydrophobic binding force or the coulomb force of attraction. Fromherz et al. suggested that the latter method can be used to incorporate a bioactive enzyme (e.g. trypsin) as a guest molecule in a host monomolecular film of an aliphatic acid or an aliphatic acid ester by means of adsorption (as described, e.g., in *FEBS Letters*, vol. 49, page 329 (1975)). The latter method can also be used to adsorb a viable protein on a monomolecular film which is subsequently applied to cover a substrate, as described in Japanese Patent Application (OPI) No. 251930/85 (FR 8407213) (the term "OPI" used herein means a published unexamined Japanese patent application). However, the monomolecular films in which functional guest molecules are supported by these adsorption or complex-forming techniques have the disadvantage that the guest molecules are readily detached from the film by washing with water or by other factors since they are supported on the monomolecular films merely by means of chemical equilibria of adsorption or complex association. If a chemical reaction is to be carried out on the monomolecular film by utilizing the catalytic activity or other capabilities of the guest molecules, a great disadvantage in practical application arises, such as lowered reactivity due to the desorption of the guest molecules during reaction. The above methods have the additional disadvantage that the capabilities of the guest molecules are not fully exhibited because the functional groups in the guest molecules are either randomly oriented on the surface of the monomolecular film or buried between the host molecules in the monomolecular film.

SUMMARY OF THE INVENTION

An object, therefore, of the present invention is to provide a reactive monomolecular or multi-layered film capable of fixing functional guest molecules at high density on the surface thereof by means of chemical bonding and which has on the surface thereof a uniform and dense arrangement of reactive functional groups that are useful for chemically binding to the guest molecules.

Another object of the present invention is to provide a functional thin organic membrane which has a water-soluble functional guest compound chemically bound at high density to the surface of a reactive monomolecular or multi-layered film of the functional thin organic membrane.

These and other objects of the present invention can be attained by a functional thin organic membrane which may comprise the following embodiments (1) a monomolecular film which contains at least one organic amphoteric host molecule having a reactive functional group capable of chemically binding with a nucleophilic functional group at room temperature; (2) a multi-layered film containing at least one organic host molecule on the outermost molecular layer; or (3) a film which is formed by chemically binding at least one water-soluble guest compound having a nucleophilic functional group to the surface of the monomolecular film or multi-layered film.

The thin organic membrane of the present invention provides a maximum density of reactive functional groups on its surface (namely, such reactive functional groups are present at a maximum surface concentration). In addition, these functional groups are all exposed on the surface of the membrane so as to impart a sufficiently high reactivity to the thin organic membrane to render it useful as a functional thin membrane.

DETAILED DESCRIPTION OF THE INVENTION

Figure 1:
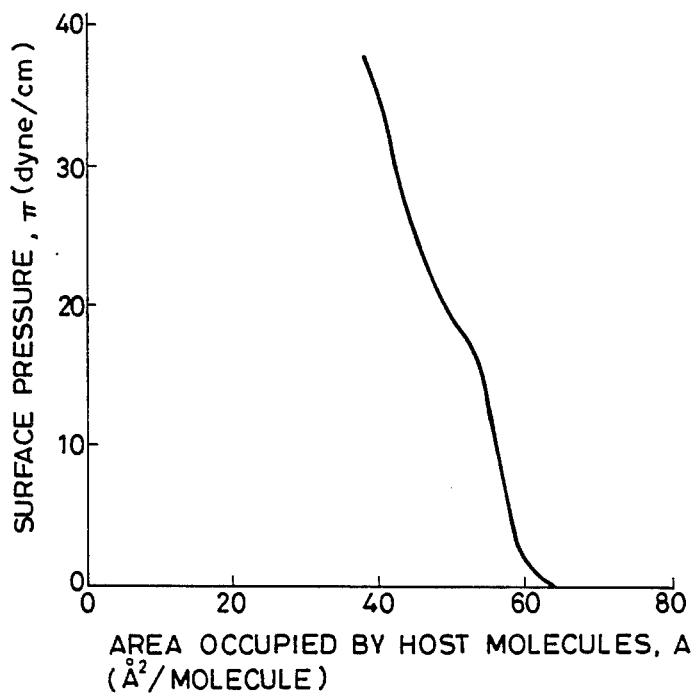
FIGS. 1 and 2 are graphs showing the relationship between the area (A) occupied by host molecules (plotted on the x-axis) and the surface pressure ($\pi$) of a monomolecular film (plotted on the y-axis).

The monomolecular film forming compound used in the present invention (this compound is hereinafter sometimes referred to as a host compound) has at least one functional group which is capable of reacting with a nucleophilic functional group. This host compound is also an amphoteric surfactant type molecule which is substantially insoluble in water and which contains both hydrophilic and hydrophobic groups. This host compound is capable of forming a stable monomolecular film on the surface of water either by itself or in the presence of other surface active molecules. The host compound may contain in its molecule a group which is active for polymerization reaction, such as an unsaturated carbon bond.

Preferably, the host compound used in the present invention is represented by formula (1):

$$(A)_m\text{—L—}(B)_n \tag{1}$$

wherein A represents a functional group capable of binding with a nucleophilic functional group at room temperature; L represents a single bond or a group having a valence of (m+n); B represents an organic residual group which imparts a monomolecular film forming ability to the compound of formula (1); and m and n are each an integer of from 1 to 3.

More preferably, the functional group represented by A capable of binding with a nucleophilic functional group at room temperature is represented by one of formulae (2) to (8):

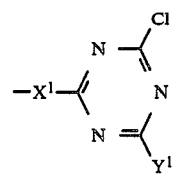
(2)

wherein $X^1$ represents

or —N—; $Y^1$ represents a hydrogen atom, —O—$R^2$ or

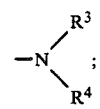

$R^1$ represents a hydrogen atom, an alkyl group having from 1 to 10 carbon atoms, an aryl group having from 6 to 10 carbon atoms, or an aralkyl group having from 7 to 10 carbon atoms; $R^2$ is either the same as $R^1$ or represents an alkali metal atom or an ammonium ion; $R^3$ and $R^4$, which may be the same or different, each has the same meaning as defined for $R^1$, provided that $R^3$ and $R^4$ may combine to form a ring;

$$-X^2-CH=CH_2 \tag{3}$$

wherein $X^2$ represents —CO—, —SO—, or —SO$_2$—;

$$-X^3-CH_2CH_2-Y^2 \tag{4}$$

wherein $X^3$ represents —CO—, —SO or —SO$_2$—; and $Y^2$ represents a group capable of being released as a result of a $\beta$-elimination reaction upon contact with a base;

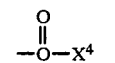
(5)

wherein $X^4$ represents a group capable of being released as a result of a substitution reaction upon reaction with a primary amino group, and may be exemplified by the following:

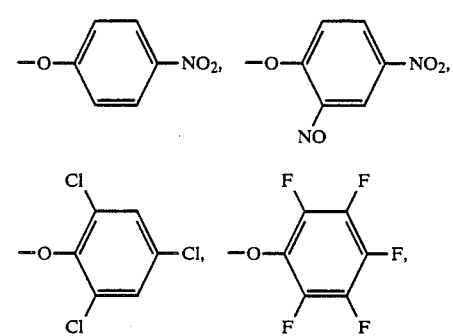

-continued

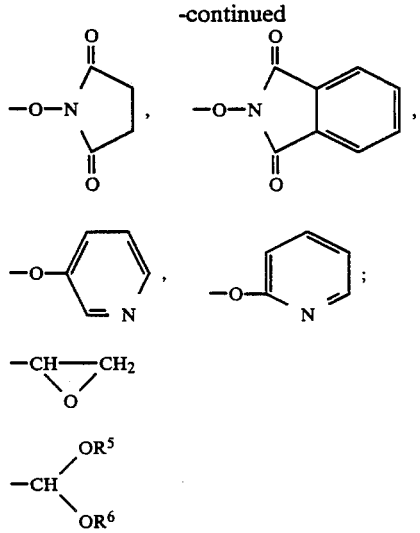

(6)
—CH——CH₂
    \ /
     O (7)
       OR⁵
      /
—CH
      \
       OR⁶ wherein $R^5$ and $R^6$ each represents an alkyl group having from 1 to 10 carbon atoms, an aryl group having from 6 to 10 carbon atoms, or an aralkyl group having from 7 to 10 carbon atoms; $R^5$ and $R^6$ may be the same or different and may combine with each other to form a ring; and

—CHO . (8)

Among the examples of A listed above, A is preferably represented by formula (2), (3), (5) or (8), with formula (2), (3) or (8) being more preferred, and formula (2) or (3) being particularly preferred. If A is represented by formula (5) or (8), a preferred embodiment is such that a water-soluble guest compound having nucleophilic functional groups is bonded to the surface of a monomolecular film or a multi-layered film.

L in formula (1) represents either a single bond or a group of a valence of (m+n). When both m and n are 1, L is preferably a divalent group selected from among an alkylene group, an arylene group, an alkenylene group, an alkynylene group, —O—, —S—,

—N—,
     |
     R¹

—CO—, —SO—, —SO₂—, and

—Si—
      /    \
    R⁷      R⁸ any of which may be present individually or in combination, wherein $R^7$ and $R^8$, which may be the same or different, are each represent a hydrogen atom, an alkyl group having from 1 to 10 carbon atoms, an aryl group having from 6 to 10 carbon atoms, or an aralkyl group having from 7 to 10 carbon atoms.

B in formula (1) represents an organic residual group which imparts a monomolecular film forming ability to the compound of formula (1) and this residual group preferably has from 10 to 30 carbon atoms. Preferred examples of the group represented by B include an aliphatic group and an aromatic group, and more preferably a long-chain alkyl group. The organic residual group represented by B may contain a functional group capable of entering into a polymerization reaction upon exposure to radiation such as ultraviolet rays, visible light, X-rays, β-rays and γ-rays, and B may be partially substituted by a hydrophilic group if this is desired for film-forming purposes.

The following are illustrative host compounds which are useful in the present invention but it should be understood that the scope of the present invention is by no means limited by these examples.

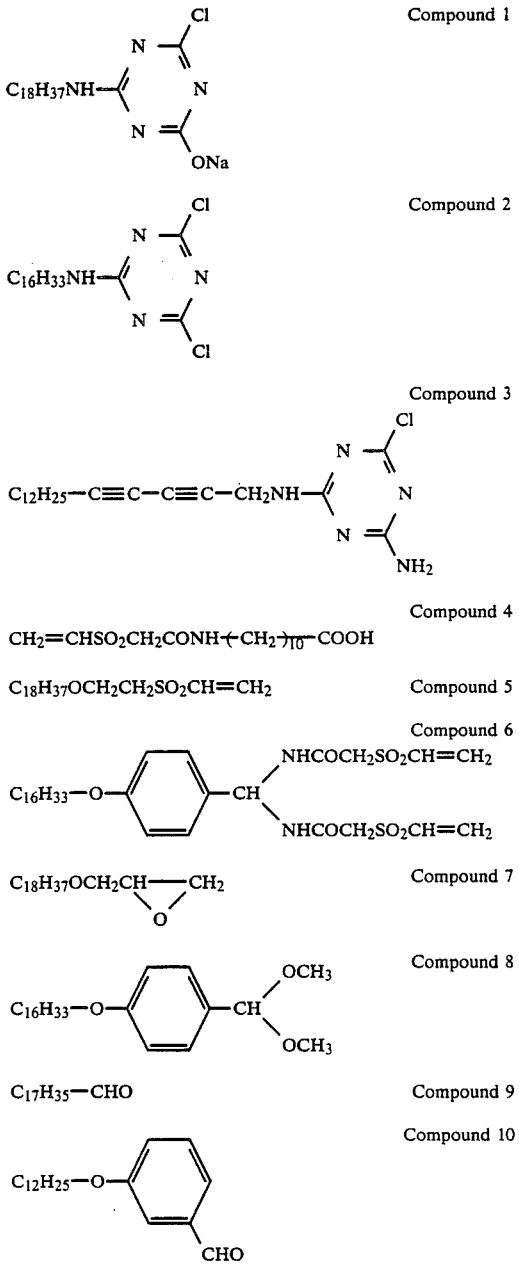

In the present invention, the monomolecular film or the multi-layered film may be formed on a substrate by the Langumuir-Blodgett method noted above, and a variety of substrate materials may be used, such as electric conductors (e.g., metals), glassy inorganic materials (e.g., glass and quartz glass), other inorganic insulators, various inorganic and organic crystals, inorganic semiconductors (e.g., $SnO_2$, $In_2O_3$, ZnO, $TiO_2$, $WO_3$, GaAs, and Si), organic semi-conductors, organic electric conductors, organic polymers, and composites of these materials. The substrate may comprise a material that serves as an electrode for establishing a connection to an external electric circuit. The surface of the substrate may be rendered hydrophilic or hydrophobic by a suitable physical or chemical treatment.

In the present invention, a monomolecular film on the surface of water can be transferred to the substrate by a variety of techniques encompassed by the known Langumuir-Blodgett process. Illustrative techniques are the vertical deposition, horizontal deposition and whirl deposition methods (see, for example, Japanese Patent Application (OPI) Nos. 189929/85 and 42394/86). A multilayered film can be formed by repeating the procedures for covering the substrate with a monomolecular film. A continuous build-up method of the type described in Japanese Patent Application (OPI) No. 209245/85 may be employed to make such a multi-layered film. In producing a multi-layered film, the host compound used in the present invention must be incorporated in the outermost molecular layer but molecular layers closer to the substrate may be formed of either the host compound or another surfactant type compound or both.

For detailed information about the Langumuir-Blodgett process, see, for example, *Zairyo Gijutsu* (Materials Technology) by K. Fukuda, vol. 4, page 261, 1986.

In the present invention, the amphoteric organic host compound having functional groups which bind with nucleophilic functional groups is allowed to bind chemically with a water-soluble organic guest compound having nucleophilic functional groups, and two typical methods can be used for such chemical binding. In the first method, a monomolecular film of the host compound is formed on the surface of water, and following the addition of a nucleophilic guest compound to the bulk of the aqueous phase (alternatively, a monomolecular film of the host compound may be formed after the addition of a guest compound to the bulk of the aqueous phase), a chemical reaction is allowed to occur at the interface between the monomolecular film and the aqueous phase under suitable temperature and time conditions (preferably at 50° C. or less, more preferably at 35° C. or less, for 5 minutes or more) and, after completion of the reaction, the resulting composite monomolecular film is transferred to a substrate. In the second method, a monomolecular film of the host compound that has been formed on the surface of water is transferred to a substrate and after being dried, the substrate is immersed in a suitable aqueous solution of a guest compound so as to effect a chemical reaction at the interface between the substrate (carrying thereon the monomolecular film of host compound) and the aqueous phase.

A variety of solvents may be used in the present invention for assisting in the spreading or dispersion of a monomolecular film and illustrative examples are commonly employed nonpolar organic solvents such as chloroform, dichloromethane, benzene, toluene and ether, as well as mixtures thereof with polar aqueous solvents such as alcohols and water.

In addition to buffer solutions having various pH values, aqueous solutions of salts of various metals such as calcium, barium and cadmium may be employed as an aqueous phase (subphase) for the formation of a monomolecular film in the present invention. The temperature of the subphase may be controlled to be either low or high if desired. During the formation and accumulation of monomolecular films, both an individual monomolecular film and the subphase may be treated with electromagnetic radiation in order to promote the interfacial chemical reaction. Preferred electromagnetic radiations include ultraviolet rays, visible light, infrared rays and microwaves. Radioactive rays such as X-rays, $\beta$-rays and $\gamma$-rays may also be used.

When the guest compound in the subphase is allowed to react chemically with the monomolecular film of host compound on the surface of water, the surface pressure of such a monomolecular film may be adjusted to any desired value but a preferred surface pressure is within a region of the isotherm between the surface pressure, $\pi$ (dyn/cm), exerted by the host molecules and the area occupied by the molecules, A (Å$^2$/molecule) where the molecule decay pressure is not reached but the value at which the surface pressure starts to rise sharply is exceeded.

The organic compounds (host compounds) having reactive functional groups which comprises the organic thin film of the present invention may have chemical bonds between adjacent molecules, or alternatively, such molecules may be polymerized with one another. Chemical bonds may be introduced into the host compound by applying heat or electromagnetic radiation to the monomolecular film of host compound formed on the surface of water; alternatively, chemical bonds may be introduced by similar methods after a plurality of monomolecular films have been built up on the substrate.

According to the present invention, a functional guest compound is chemically bonded to the surface of the monomolecular film or the multi-layered film. While any compounds having desired functions may be employed as the guest compounds, preferred examples are physiologically active substances such as enzymes, proteins, antigens and antibodies, and light-sensitive compounds such as dyes and pigments. These guest compounds have at least one nucleophilic functional group such as an amino, hydroxyl or carboxyl group. Among the types of guest compounds examplified above, enzymes are particularly preferred in that they are capable of achieving binding reactions with high efficiency. Illustrative enzymes include: oxidative enzymes such as glucose oxidase, cholesterol oxidase, uricase, and choline oxidase; hydrogen removing enzymes such as alcohol dehydrogenase, glycerol dehydrogenase, glucose-6-phosphate dehydrogenase, and glutamic acid dehydrogenase; and other analytical enzymes such as peroxidase, urease, lipoprotein lipase, diaphorase, catalase, kinases, and cholesterol esterase.

Preferred guest compounds which are antigens and antibodies include immunoglobulin G and many other substances, such as those shown systematically in *Men-'eki no Kenkyu* (Study of Immune System), edited by Y. Yamamura and published by Dobun Shoin, 1986.

The reactivity of the thin organic membrane of the present invention can be advantageously utilized to chemically fix or immobilize desired functional compounds (e.g., enzymes and proteins) on the surface of the membrane. These functional compounds either undergo chemical reactions (e.g., catalytic reactions, photochemical reactions, and oxidation-reduction reactions) with high efficiency or cause physical changes (e.g., optical changes and electrical changes), and these chemical reactions or physical changes can be utilized for various purposes such as sensor image formation, information recording, and energy conversion. Therefore, the thin organic membrane of the present invention is expected to find great utility in commercial applications.

The following examples are provided for the purpose of further illustrating the present invention but are in no way to be taken as limiting the scope thereof.

EXAMPLE 1

Compound 6 hereinabove was dissolved in a mixed solvent of methylene chloride and dimethylformamide to make a solution at a concentration of $5 \times 10^{-3}$ mol/l. Twenty microliters of this solution was spread over the surface of a neutral phosphate buffer ($10^{-3}$ mol/l) in a water tank ($20 \times 40 \times 7$ cm; true capacity, 5 l) for monomolecular film formation, and the solvent was evaporated to prepare a monolayer of Compound 6. The monomolecular film on the surface of water was compressed with a motor-driven barrier at a rate of 50 cm$^2$/min. Measurements at room temperature of the surface pressure, $\pi$ (dyn/cm), exerted by the monolayer produced an isotherm of surface pressure $\pi$ vs. the area occupied by host molecules A (Å$^2$/molecule) as shown in FIG. 1.

After the monomolecular film was controlled to have a constant surface pressure of 15 dyn/cm, an aqueous solution of glucose oxidase (GOD) was added to the bulk of the subphase in such an amount that the concentration of GOD in the subphase would be $10^{-10}$ mol/l. The monomolecular film was thereafter left to stand at room temperature for 20 minutes with its surface pressure controlled at 15 dyn/cm.

In the next step, a quartz glass substrate, the surface of which has been rendered hydrophobic by treatment with a solution of trimethyl chlorosilane in toluene, was placed in horizontal contact with the monomolecular film on the surface of water in such a way that it would be covered with a single layer of the monomolecular film.

When the absorption spectrum of the substrate was measured, an absorption peak occurred at 280 nm. Since this peak was characteristic of enzymes, it was established that GOD had been supported on the monomolecular film on the substrate. This absorption peak was only slightly affected even when the surface of the substrate was washed by its immersion in a phosphate buffered aqueous solution (pH, 7.0) containing 2 mol/l of NaCl, so it was also found that GOD fixed on the substrate was stable.

EXAMPLE 2

Figure 2:
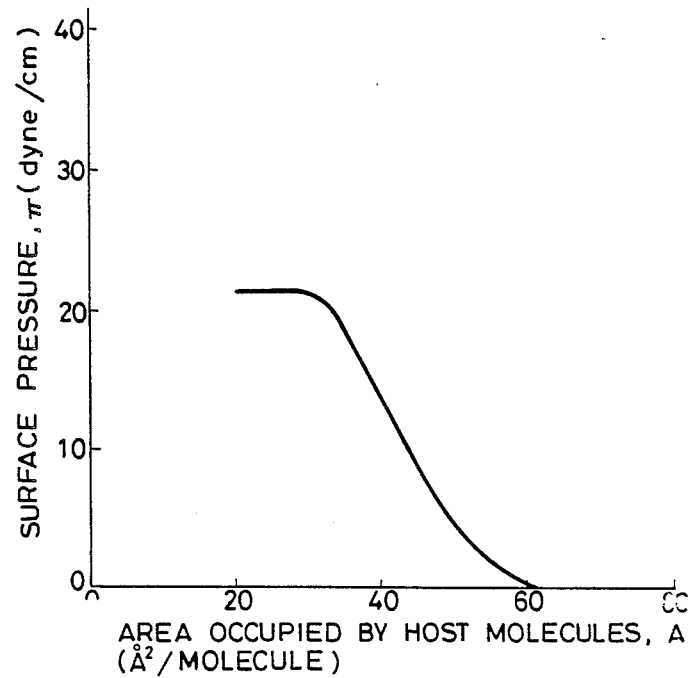

Compound 10 having a reactive aldehyde group was dissolved in methylene chloride to form a solution having a concentration of $5 \times 10^{-3}$ mol/l. Twenty microliters of the solution were spread to form a monomolecular film of Compound 10 over the surface of a neutral phosphate buffer solution ($10^{-3}$ mol/l) in a water tank for monomolecular film formation. The monomolecular film was compressed as in Example 1 at a constant rate, thereby producing a $\pi$-A profile as shown in FIG 2.

After the monomolecular film was compressed to a surface pressure of 15 dyn/cm, a neutral aqueous solution of trypsin was added to the bulk of the subphase in such an amount that the concentration of trypsin in the subphase was $10^{-5}$ mol/l. The monomolecular film was thereafter left to stand at room temperature for 20 minutes with its surface pressure controlled at 15 dyn/cm.

As in Example 1, the monomolecular film was transferred onto a hydrophobic quartz glass substrate, which was subsequently rinsed with a phosphate buffered neutral aqueous solution containing 2 mol/l of NaCl. The thus prepared enzyme-carrying functional thin organic film on the substrate was immersed in a neutral phosphate buffer solution (35° C.) containing 1 wt % of casein so that the enzyme would undergo polypeptide decomposition reaction on casein. No precipitate formed in the reaction solution even when 5 wt % trichloroacetic acid was added. This fact, combined with the results of absorbance measurement at 280 nm and analysis by the Lowry method, established that oligopeptides were produced as a result of highly efficient conversion from casein.

While the invention has been described in detail and with reference to specific examples thereof, it will be apparent to one skilled in the art that various changes and modifications can be made therein without departing from the spirit and scope thereof.

What is claimed is:

1. A functional thin organic membrane comprising a monomolecular film which contains at least one organic amphoteric host molecule having a reactive functional group capable of chemically binding with a nucleophilic functional group at room temperature, wherein said at least one organic amphoteric host molecule is represented by formula (1)

(A)$_m$—L—(B)$_n$     (1)

wherein A represents a functional group capable of binding with a nucleophilic functional group at room temperature; L represents a single bond or a group having a valence of (m+n); B represents an organic residual group which imparts a monomolecular film forming ability to the compound of formula (1); and m and n are each an integer of from 1 to 3, and wherein said functional group represented by A is represented by one of formulae (2) to (6):

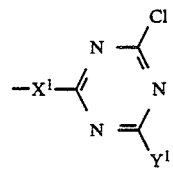
(2)

wherein X$^1$ represents

or —N—; Y$^1$ represents a hydrogen atom, —O—R$^2$ or

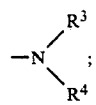

R$^1$ represents a hydrogen atom, an alkyl group having from 1 to 10 carbon atoms, an aryl group having from 6 to 10 carbon atoms, or an aralkyl group having from 7 to 10 carbons atoms; R$^2$ is either the same as $R^1$ or represents an alkali metal atom or an ammonium atom; $R^3$ and $R^4$, which may be the same or different, each has the same meaning as defined for $R^1$, provided that $R^3$ and $R^4$ may combine to form a ring:

$$-X^2-CH=CH_2 \tag{3}$$

wherein $X^2$ represents $-CO-$, $-SO-$, or $-SO_2-$;

$$-X^3-CH_2CH_2-Y^2 \tag{4}$$

wherein $X^3$ represents $-CO-$, $-SO-$, or $-SO_2-$; and $Y^2$ represents a group capable of being released as a result of a $\beta$-elimination reaction upon contact with a base;

$$\underset{\underset{O-X^4}{\|}}{O} \tag{5}$$

wherein $X^4$ represents a group capable of being released as a result of a substitution reaction upon reaction with a primary amino group; and

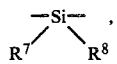
(6)

2. A functional thin organic film as claimed in claim 1, wherein said reactive functional group represented by (A) is selected from the group consisting of a substituted cyanuric group, and an active vinyl group.

3. A functional thin organic membrane as in claim 1, wherein L is a divalent group selected from among an alkylene group, an arylene group, an alkenylene group, an alkynylene group, $-O-$, $-S-$, $-NR_1-CO-$, $-SO-$, $-SO_2-$, and $$\underset{R^7 \quad R^8}{\overset{-Si-}{\diagup \diagdown}},$$

any of which may be present individually or in combination, wherein $R^7$ and $R^8$, which may be the same or different, each represent a hydrogen atom, an alkyl group having from 1 to 10 carbon atoms, an aryl group having from 6 to 10 carbon atoms, or an aralkyl group having from 7 to 10 carbon atoms.

4. A functional thin organic membrane as in claim 1, wherein said organic residual group which imparts a monomolecular film forming ability to said host compound, has from 10 to 30 carbon atoms, and may contain a functional group capable of entering into a polymerization reaction upon exposure to radiation, and may be partially substituted by a hydrophilic group.

5. A functional thin organic membrane as in claim 1, wherein said membrane comprises a multi-layered film, and said monomolecular film is located on the outermost layer of said multilayered film.

6. A functional thin organic membrane as in claim 7, wherein said monomolecular film or said multi-layered film is formed on a substrate, said substrate material being selected from the group consisting of electric conductors, glassy inorganic materials, other inorganic insulators, organic crystals, inorganic crystals, organic semi-conductors, inorganic semi-conductors, organic electric conductors, organic polymers, and composites of said substrate materials.

7. A functional thin organic membrane as in claim 5, wherein the multilayered film contains at least one other monomolecular film which contains at least one organic amphoteric host molecule having a reactive functional group capable of chemically binding with a nucleophilic functional group at room temperature.

8. A functional thin organic membrane as in claim 1, further comprising at least one water-soluble organic guest compound having a nucleophilic functional group which is chemically bonded to said at least one host molecule having a reactive functional group.

9. A functional thin organic membrane as in claim 8, wherein said at least one water-soluble organic guest compound is a physiologically active substance.

10. A functional thin organic membrane as in claim 9, wherein said physiologically active substance is selected from among enzymes, proteins, antigens, and antibodies.

11. A functional thin organic membrane as in claim 8, wherein said at least one water-soluble organic guest compound is a light-sensitive compound.

12. A functional thin organic membrane as in claim 8, wherein said nucleophilic functional group is an amino group, a hydroxyl group or a carboxyl group.

13. A functional thin organic membrane as in claim 1, wherein said reactive functional groups are present on the surface of said membrane at a maximum surface concentration to provide high reactivity.

14. A functional thin organic membrane as in claim 1, wherein said organic amphoteric host molecule is substantially water-insoluble and contains both hydrophilic and hydrophobic groups.

15. A functional thin organic membrane as in claim 1, wherein said monomolecular film is formed on the surface of an aqueous medium.

16. A functional thin organic membrane as in claim 15, wherein a nucleophilic guest compound is added to the aqueous medium whereby a chemical reaction occurs at the interface between the monomolecular film and the aqueous medium, said guest compound being chemically bonded to said host compound.

17. A functional thin organic membrane as in claim 1, wherein A is represented by formula (2).

18. A functional thin organic membrane as in claim 1, wherein A is represented by formula (3).

* * * * *